US008977390B2

(12) United States Patent
Jefferies et al.

(10) Patent No.: US 8,977,390 B2
(45) Date of Patent: Mar. 10, 2015

(54) SYSTEMS AND METHODS FOR DISPENSING BENEFICIAL PRODUCTS

(75) Inventors: Trent Jefferies, South Jordan, UT (US); David Frey, Salt Lake City, UT (US); Galen Earl Murdock, Salt Lake City, UT (US); Mary Schwartz, Salt Lake City, UT (US); Samantha Jefferies, Dana Point, CA (US)

(73) Assignee: Vendrx, Inc., Salt Lake City, UT (US)

( * ) Notice: Subject to any disclaimer, the term of this patent is extended or adjusted under 35 U.S.C. 154(b) by 329 days.

(21) Appl. No.: 13/593,292

(22) Filed: Aug. 23, 2012

(65) Prior Publication Data

US 2013/0231775 A1    Sep. 5, 2013

Related U.S. Application Data

(60) Provisional application No. 61/526,627, filed on Aug. 23, 2011, provisional application No. 61/555,397, filed on Nov. 3, 2011.

(51) Int. Cl.
*G06Q 10/10*  (2012.01)
*G06F 19/00*  (2011.01)
*G06Q 50/22*  (2012.01)
(Continued)

(52) U.S. Cl.
CPC ............ *G06F 19/3462* (2013.01); *G06Q 50/22* (2013.01); *G07F 17/0092* (2013.01); *G06Q 10/087* (2013.01); *G06Q 10/10* (2013.01)
USPC ........................................................ 700/237

(58) Field of Classification Search
CPC .. G07F 17/0092; G06Q 10/087; G06Q 10/10; G06Q 50/22; G06F 19/3462

USPC .................................. 700/236, 237, 240, 241
See application file for complete search history.

(56) References Cited

U.S. PATENT DOCUMENTS 6,438,451 B1 *   8/2002   Lion ............................ 700/237
6,529,801 B1 *   3/2003   Rosenblum ................... 700/237
(Continued)

FOREIGN PATENT DOCUMENTS

| KR | 10-2008-0090505 | 10/2008 |
| WO | WO-2007-041767 A1 | 4/2007 |
| WO | WO-2008-143757 A1 | 11/2008 |

OTHER PUBLICATIONS

WIPO, International Search Report and Written Opinion for PCT/US2012/052110, mailed Feb. 26, 2013.
(Continued)

*Primary Examiner* — Timothy Waggoner
(74) *Attorney, Agent, or Firm* — Stoel Rives LLP (57) ABSTRACT

A dispensing station comprises beneficial products for patients of a health care provider. An inventory database tracks inventory available in the dispensing station. A patient is associated with a prescription record, which specifies a prescribed beneficial product. The patient may provide patient identifying information to the dispensing station, such as credentialed payment information, which may be used to identify a prescription record, authenticate the patient, transfer a payment, and/or dispense the prescribed beneficial product to the patient. The prescription record may be valid for a limited time period, may be restricted to fulfillment within a particular location, and/or may be restricted to one or more specified dispensing stations. The dispensing station may validate the beneficial products before dispensing the products to the patient.

19 Claims, 8 Drawing Sheets

(51) Int. Cl.
    *G07F 17/00*    (2006.01)
    *G06Q 10/08*    (2012.01)

(56) References Cited

U.S. PATENT DOCUMENTS

| | | | |
|---|---|---|---|
| 6,631,826 B2 | 10/2003 | Pollard et al. |
| 6,697,704 B2 | 2/2004 | Rosenblum |
| 6,766,218 B2 | 7/2004 | Rosenblum |
| 6,892,941 B2 | 5/2005 | Rosenblum |
| 6,971,541 B2 | 12/2005 | Williams et al. |
| 6,971,544 B2 | 12/2005 | Williams et al. |
| 6,974,049 B2 | 12/2005 | Williams et al. |
| 6,974,050 B2 | 12/2005 | Williams et al. |
| 6,982,941 B2 | 1/2006 | Yamanoi et al. |
| 7,006,893 B2 | 2/2006 | Hart et al. |
| 7,080,755 B2 | 7/2006 | Handfield et al. |
| 7,118,006 B2 | 10/2006 | Williams et al. |
| 7,123,989 B2 | 10/2006 | Pinney |
| 7,228,200 B2 | 6/2007 | Baker et al. |
| 7,260,402 B1 | 8/2007 | Ahmed |
| 7,263,411 B2 | 8/2007 | Shows et al. |
| 7,275,353 B2 | 10/2007 | Williams et al. |
| 7,289,879 B2 | 10/2007 | William et al. |
| 7,344,049 B2 | 3/2008 | Daniels et al. |
| 7,374,625 B2 | 5/2008 | Panetta et al. |
| 7,410,098 B2 | 8/2008 | Denenberg et al. |
| 7,440,818 B2 | 10/2008 | Handfield et al. |
| 7,444,203 B2 | 10/2008 | Rosenblum |
| 7,469,820 B2 | 12/2008 | Rosenblum |
| 7,471,993 B2 | 12/2008 | Rosenblum |
| 7,537,155 B2 | 5/2009 | Denenberg et al. |
| 7,555,362 B2 | 6/2009 | Broussard et al. |
| 7,565,782 B2 | 7/2009 | Williams et al. |
| 7,565,784 B2 | 7/2009 | Williams et al. |
| 7,565,785 B2 | 7/2009 | Sink et al. |
| 7,581,373 B2 | 9/2009 | Sink et al. |
| 7,584,018 B2 | 9/2009 | Shows et al. |
| 7,596,932 B2 | 10/2009 | Sink et al. |
| 7,630,788 B1 * | 12/2009 | Reese ............... 700/216 |
| 7,630,790 B2 | 12/2009 | Handfield et al. |
| 7,668,998 B2 | 2/2010 | Perisich et al. |
| 7,689,318 B2 * | 3/2010 | Draper ............... 700/236 |
| 7,703,637 B2 | 4/2010 | Michelli et al. |
| 7,721,914 B2 | 5/2010 | Handfield et al. |
| 7,735,301 B2 | 6/2010 | Sink et al. |
| 7,735,681 B2 | 6/2010 | Handfield et al. |
| 7,735,683 B2 | 6/2010 | Handfield et al. |
| 7,743,943 B2 | 6/2010 | Williams et al. |
| 7,751,933 B2 | 7/2010 | Handfield et al. |
| D622,746 S | 8/2010 | Daniels et al. |
| 7,770,358 B2 | 8/2010 | Sink et al. |
| 7,774,097 B2 | 8/2010 | Rosenblum |
| 7,783,378 B2 | 8/2010 | Pinney et al. |
| 7,783,379 B2 | 8/2010 | Beane et al. |
| 7,787,986 B2 * | 8/2010 | Pinney et al. ............... 700/232 |
| D623,207 S | 9/2010 | Gentry, Jr. et al. |
| D623,208 S | 9/2010 | Parrish et al. |
| 7,797,077 B2 * | 9/2010 | Hale ............... 700/236 |
| 7,805,216 B2 | 9/2010 | Shows et al. |
| 7,832,591 B2 | 11/2010 | Karwacki, Jr. et al. |
| 7,837,061 B2 | 11/2010 | Dummer et al. |
| 7,840,307 B2 | 11/2010 | Mauger et al. |
| 7,844,362 B2 | 11/2010 | Handfield et al. |
| 7,844,363 B1 | 11/2010 | Mehdizadeh |
| 7,844,383 B2 | 11/2010 | Shinozawa et al. |
| 7,857,161 B2 | 12/2010 | Pinney et al. |
| 7,860,603 B2 | 12/2010 | Handfield et al. |
| 7,866,506 B2 | 1/2011 | Daniels et al. |
| 7,870,973 B2 | 1/2011 | Michelli et al. |
| 7,886,931 B2 | 2/2011 | Handfield et al. |
| 7,889,330 B2 | 2/2011 | Newcomb |
| 7,898,657 B2 | 3/2011 | Klein et al. |
| 7,905,372 B2 | 3/2011 | Williams et al. |
| 7,908,030 B2 | 3/2011 | Handfield et al. |
| 7,909,207 B2 | 3/2011 | Handfield et al. |
| 7,917,246 B2 | 3/2011 | Handfield et al. |
| 7,921,690 B2 | 4/2011 | Uebel et al. |
| 7,930,064 B2 | 4/2011 | Popovich, Jr. et al. |
| 7,949,426 B2 | 5/2011 | Handfield et al. |
| 7,949,427 B2 | 5/2011 | Michelli et al. |
| D639,322 S | 6/2011 | Daniels et al. |
| 7,980,419 B2 | 7/2011 | Young et al. |
| 7,988,017 B2 | 8/2011 | Kulberg et al. |
| 7,988,404 B2 | 8/2011 | Williams et al. |
| 7,990,526 B2 | 8/2011 | Newcomb |
| 7,992,365 B2 | 8/2011 | Uebel et al. |
| 7,996,105 B2 | 8/2011 | Handfield et al. |
| 8,000,836 B2 | 8/2011 | Pinney et al. |
| 8,027,748 B2 | 9/2011 | Handfield et al. |
| 8,033,424 B2 | 10/2011 | Rosenblum |
| 8,112,175 B2 | 2/2012 | Handfield et al. |
| 8,121,725 B2 | 2/2012 | Baker et al. |
| 8,180,484 B2 | 5/2012 | Baker et al. |
| 8,190,291 B2 | 5/2012 | Beane et al. |
| 8,191,719 B2 | 6/2012 | van Ooyen et al. |
| 8,195,329 B2 | 6/2012 | Pinney et al. |
| 8,267,310 B2 | 9/2012 | Waugh et al. |
| 8,465,243 B2 | 6/2013 | van Ooyen et al. |
| 8,577,145 B2 | 11/2013 | Panetta |
| 8,695,814 B2 | 4/2014 | van Ooyen et al. |
| 8,738,177 B2 | 5/2014 | van Ooyen et al. |
| 2006/0117162 A1 | 6/2006 | Sauber |
| 2008/0179387 A1 | 7/2008 | Cantlay et al. |
| 2008/0235519 A1 | 9/2008 | Onouchi et al. |
| 2009/0048712 A1 | 2/2009 | Rosenblum |
| 2010/0051187 A1 | 3/2010 | Willick et al. |
| 2010/0145506 A1 | 6/2010 | Waugh et al. |
| 2010/0198401 A1 | 8/2010 | Waugh et al. |
| 2010/0264158 A1 | 10/2010 | van Ooyen et al. |
| 2010/0268380 A1 | 10/2010 | Waugh et al. |
| 2010/0324728 A1 | 12/2010 | Rosenblum |
| 2011/0014018 A1 | 1/2011 | van Ooyen et al. |
| 2011/0017764 A1 | 1/2011 | Liguori |
| 2011/0036856 A1 | 2/2011 | van Ooyen et al. |
| 2011/0150346 A1 | 6/2011 | Panetta |
| 2011/0192893 A1 | 8/2011 | Waugh et al. |
| 2011/0204144 A1 | 8/2011 | Waugh et al. |
| 2011/0229296 A1 | 9/2011 | van Ooyen et al. |
| 2011/0231010 A1 | 9/2011 | Panetta et al. |
| 2011/0288880 A1 | 11/2011 | Waugh |
| 2012/0004770 A1 | 1/2012 | van Ooyen et al. |
| 2012/0061338 A1 | 3/2012 | Willick et al. |
| 2012/0083666 A1 | 4/2012 | Waugh et al. |
| 2013/0140257 A1 | 6/2013 | van Ooyen et al. |
| 2013/0204432 A1 | 8/2013 | Panetta et al. |
| 2013/0251479 A1 | 9/2013 | Waugh et al. |

OTHER PUBLICATIONS

International Search Report and Written Opinion issued in PCT/US2012/063561 on Mar. 19, 2013.

* cited by examiner

SYSTEMS AND METHODS FOR DISPENSING BENEFICIAL PRODUCTS

CROSS-REFERENCE TO RELATED APPLICATIONS

This application claims priority to U.S. Provisional Patent Application Ser. No. 61/526,627 entitled, "Systems and Methods for Dispensing Beneficial Products," filed Aug. 23, 2011, and to U.S. Provisional Patent Application Ser. No. 61/555,397 entitled, "Systems and Methods for a Beneficial Product Dispenser," filed Nov. 3, 2011, each of which is hereby incorporated by reference in its entirety.

TECHNICAL FIELD

This disclosure relates to systems and methods for dispensing beneficial products, such as pharmaceuticals to a patient.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

Health care providers are facing rising costs and regulatory overhead in an increasingly competitive market. Health care providers may be required to maintain secure patient medical records, electronic prescriptions, and the like. Health care providers need innovative ways of offsetting these costs while still meeting the needs of their patients.

In some cases, a health care provider dispenses beneficial products, such as prescription medication, directly to its patients. The direct dispensing model provides an additional revenue stream for the health care provider and is convenient for the patients. However, direct dispensing may not be economically feasible for some health care providers due to high infrastructure and regulatory compliance costs, and the relatively low volumes involved.

Direct dispensing typically requires the health care provider to act as a "mini pharmacy" to its patients. The health care provider purchases beneficial products from a provider (e.g., manufacturer, distributor, wholesaler, etc.), which are dispensed to patients. This model is not particularly efficient for low-volume operations, however, since managing a "mini-pharmacy" involves a significant amount of work. Tasks, such as receiving, storing, securing, tracking, dispensing, regulatory compliance, adjudication, coordination of benefits, and accounting, fall to the health care provider. Although there are services available to streamline these tasks, many health care providers (particularly smaller providers) find that the services are not time and/or cost effective.

The embodiments disclosed herein may provide a turn-key solution for automated, in-office dispensing of beneficial products to patients. In some embodiments, beneficial products are dispensed from an automated dispensing machine. When the health care provider writes a prescription for a beneficial product, the patient is given the option of fulfilling the prescription using the disclosed automated dispensing system. The dispensing system provides a current inventory status, which may be used to verify that the patient's prescription can be fulfilled. The health care provider may create a prescription record for the patient, who may retrieve the beneficial products from the dispensing station. The patient may be required to authenticate his identity to the dispensing machine and/or provide payment for the dispensed beneficial products. The patient may pay for the prescription directly without adjudicating the claim with an insurance carrier or other benefit provider.

Figure 1A:
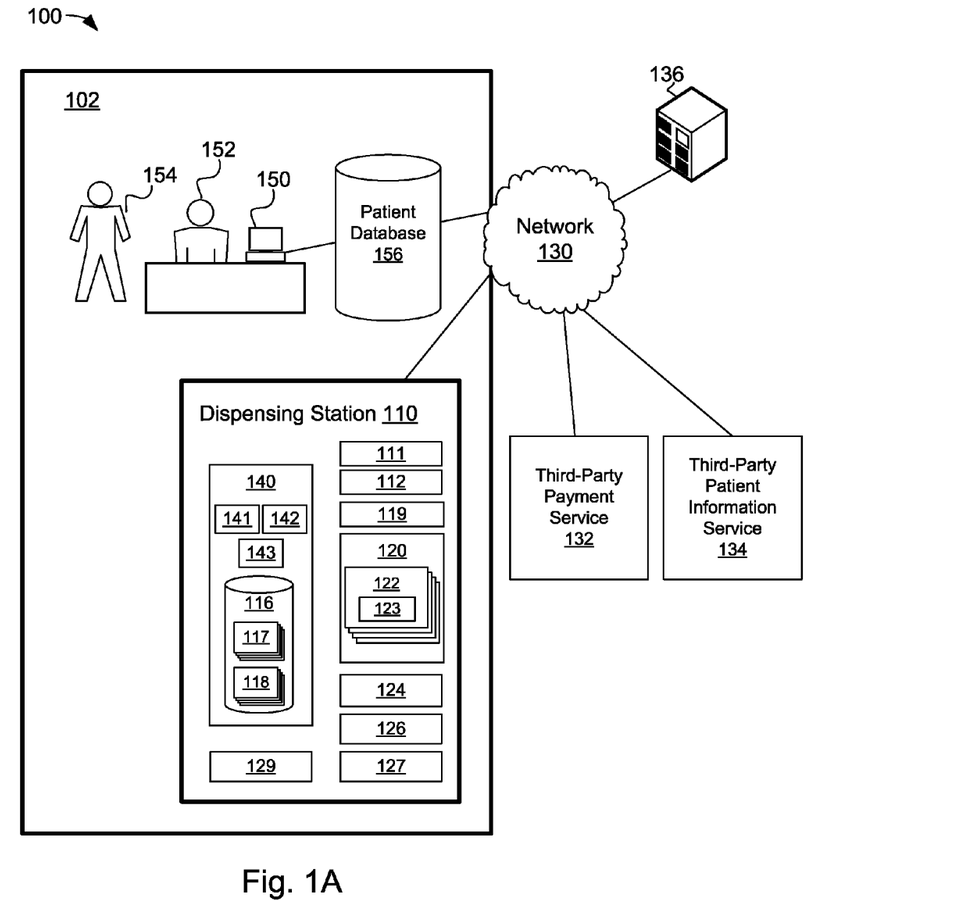
FIG. 1A is a block diagram of one embodiment of a system for dispensing beneficial products.

FIG. 1A depicts one embodiment of a system 100 for dispensing beneficial products. The system includes a dispensing station 110 located in, for example, the office 102 of a health care provider (e.g., a doctor's office). The dispensing station 110 may comprise a controller 111. The controller 111 may be configured to control the operation of the dispensing station 110 and may comprise a processor, memory, non-transitory computer-readable storage medium, and the like. The dispensing station 110 may be communicatively coupled to a network 130 using a communication interface 112. The communication interface 112 may comprise one or more wired or wireless interfaces, such as an 802.11 wireless network interface, an Ethernet interface, an Ethernet over powerline interface, a BLUETOOTH® interface, a near-field wireless communication interface, a Public Switched Telephone Network (PSTN) interface, or any other suitable communication interface. The network 130 may comprise a local area network, a public network (e.g., the Internet), or any other suitable communication network.

The dispensing station 110 may comprise and/or be communicatively coupled to an inventory database 116 that maintains information pertaining to an inventory 120 of beneficial products within the dispensing station 110. In some embodiments, the database 116 is implemented using a computing device 140 comprising a processor 141, memory 142, non-transitory storage media 143, and so on. The computing device 140 may be a component of the dispensing station 110 (e.g., located within the dispensing station 110). Alternatively, the computing device 140 (and database 116) may be implemented, in part or in full, in a separate network-accessible computing device, such a health-care provide computing system 150 or server computing device 136.

In some embodiments, the beneficial products in the inventory 120 are packaged in separately dispensable units 122, each having a respective unique identifier embodied on a unique identifier tag 123. The unique identifier may be used to track the type and/or quantity of beneficial product within each dispensable unit 122 in the inventory database 116 (using a respective record 117). The unique identifier of a dispensable unit 122 may be embodied on a unique identifier tag 123. The unique identifier tag 123 may comprise any tag capable of storing and/or conveying a unique identifier, including, but not limited to: a Radio Frequency Identifier (RFID), an optical code, such as a bar code, a near-field communication (NFC) tag, or other suitable tag. The dispensing station 110 may comprise one or more unique identifier tag reader(s) 119 that are configured to read the unique identifier tags 123 of the dispensable units 122.

The inventory database 116 associates each unique identifier with corresponding inventory information, which may include, but is not limited to: the type of beneficial product in a dispensable unit 122 (e.g., by National Drug Code (NDC), RxNorm, Universal Product Code (UPC), serial number, or other suitable identifier), the quantity of beneficial product in a dispensable unit 122, inventory status of a dispensable unit 122 (e.g., prescribed to a patient and awaiting dispensing, etc.), the age and/or expiration date of a beneficial product, the manufacturer of a beneficial product, usage and/or dosage instructions pertaining to a beneficial product, the source of a beneficial product, pricing information for the beneficial product, and so on. The inventory information may be maintained in respective records 117 of the database 116, each record 117 corresponding to a dispensable unit 122 in the dispensing station 110.

A health care provider 152 (e.g., doctor or other health care personnel) may prescribe a beneficial product to a patient 154. The patient 154 may elect to fill the prescription at the dispensing station 110. In some embodiments, database 116 may be queried to verify that the dispensing station 110 has sufficient inventory to fulfill the prescription (e.g., has beneficial products of the type and/or quantity prescribed to the patient 154). The inventory may be verified before the patient 154 is given the option of fulfilling the prescription using the dispensing station 110. Alternatively, the inventory may be verified when the patient 154 attempts to fulfill the prescription at the dispensing station 110.

If the dispensing station 110 does not have sufficient inventory, the health care provider 152 may query the inventory of other dispensing stations (not shown) via the network 130 and direct the patient 154 to fulfill the prescription at one or more alternative location(s) of the health care provider 152. Alternatively, the health care provider 152 may determine when the dispensing station 110 is scheduled to be restocked, and may direct the patient 154 to fulfill the prescription after restocking.

If the patient elects to fulfill the prescription using the dispensing station 110, a prescription record 118 representing the prescription may be created in the database 116. The prescription record 118 may include information pertaining to the prescription including, but not limited to: the type of beneficial product prescribed to the patient 154 (e.g., by NDC, RxNorm, or other identifier), the quantity and/or dosage of beneficial product prescribed to the patient 154, a patient identifier (described below), a time to live (TTL) for the prescription record, an identifier of the dispensing station (s) 110 through which the prescription may be fulfilled, and so on.

In some embodiments, the step of creating the prescription record 118 may comprise reserving inventory to fulfill the prescription. The inventory reservation may ensure that the inventory needed to fulfill the prescription is available when the patient 154 attempts to fulfill the prescription at the dispensing station 110. For example, the inventory database 116 may be updated to identify one or more dispensable units 122 needed to fulfill the prescription record 118. The dispensable units 122 may be marked as "reserved" for the patient 154 in the inventory database 116 and unavailable for other prescriptions and/or patients. Alternatively, the inventory database 116 may be updated to indicate that a particular quantity of beneficial product(s) are reserved for the patient 154 within the inventory 120 without reserving any particular dispensable units 122.

In some embodiments, the prescription record 118 includes and/or references patient identifying information that can be used to associate a patient with a prescription record and/or authenticate the identity of the patient 154. As used herein, patient identifying information may comprise any information that can be used to identify and/or authenticate a patient. Patient identifying information may comprise descriptive information, such as name, birth date, zip code, age, address, email address, phone number, or the like. Patient identifying information may further comprise one or more credentials established by the patient 154, such as a password, personal identification number (PIN), the answer to a "secret question" (e.g., street you grew up on), or the like. Patient identifying information may comprise and/or relate to credentialed payment information provided by the patient 154 (discussed below). In some embodiments, patient identifying information may further comprise biometric information, such as a fingerprint, iris scan, voice sample, facial recognition, or the like. The biometric information may be acquired by one or more measurement devices (not shown) of the dispensing station 110 and/or health care provider 152.

Patient identifying information may be entered by a health care provider 152 when the prescription is issued. Alternatively, or in addition, patient identifying information may be referenced in one or more of: a patient database 156 maintained by the health care provider 152, the database 116, a third-party payment service 132, a third-party patient information service 134, an identity service, such as Microsoft Cardspace®, OpenID®, etc., or the like.

The patient 154 may fulfill the prescription using the dispensing station 110. Fulfilling the prescription may comprise the patient 154 providing a payment, and receiving the prescribed beneficial products from the inventory 120 of the dispensing station 110.

In some embodiments, the dispensing station 110 comprises a fulfillment module 124 that is configured to process prescriptions for patients 154. The fulfillment module 124 may be configured to fulfill prescriptions for patients 154, which may comprise identifying prescription record(s) 118 of a patient 154, authenticating the identity of the patient 154, processing a payment from the patient 154, and so on. In some embodiments, processing the payment comprises receiving credentialed payment information from the patient 154. As used herein, credentialed payment information refers to any information related to a payment transaction, which may include, but is not limited to, credit card information, debit card information, banking information, checking account information, electronic payment information, such as a PAYPAL® credential, or other suitable payment-related information. In such embodiments, the credentialed payment information may be comprised of, or may be used to generate, the patient identifying information.

Alternatively, or in addition, the payment may be made using a currency transaction, or any other suitable form of payment. Accordingly, the fulfillment module 124 may comprise one or more payment receiving modules 126, such as currency receivers, card readers (e.g., magnetic strip readers), near-field communication (NFC) devices, text input devices, or other suitable input devices.

The fulfillment module 124 may be configured to identify the prescription record 118 of the patient 154 using information provided by the patient 154. In some embodiments, the fulfillment module 124 compares credentialed payment information provided by the patient 154 to pay for the prescription (if any), to patient identifying information included within and/or referenced by one or more prescription records 118, as described above. For example, the fulfillment module 124 may compare a credit card number, billing address, name, or other credentialed payment information to information within and/or referenced by one or more prescription records 118. Alternatively, or in addition, the payment transaction may comprise a dedicated authentication step. For example, when paying by PAYPAL®, the patient 154 may enter a user identifier and/or password, which may be used to authenticate the patient's identity to the payment system; this information may be leveraged by the fulfillment module 124 to identify the prescription record 118 of the patient 154 and/or authenticate the patient 154.

In some embodiments, the fulfillment module 124 is configured to acquire patient identifying information instead of and/or in addition to the credentialed payment information described above. The fulfillment module 124 uses the acquired information to identify the prescription record 118 associated with the patient 154 (if any). The fulfillment module 124 may leverage the acquired information to authenticate identity of the patient 154 and/or verify that the patient is authorized to fulfill the prescription. The fulfillment module 124 may authenticate the patient 154 by comparing information acquired from the patient 154 to patient identifying information within and/or referenced by the prescription record 118. The patient identifying information may include any of the patient identifying information described above (e.g., name, birth date, password, etc.). The patient 154 may be prompted to provide patient identifying information via one or more human-machine interface (HMI) components 127 of the dispensing station 110, which may include, but are not limited to: display devices, keyboard inputs, touch screen inputs, biometric measurement devices (e.g., fingerprint reader, iris scanner, etc.), card readers, or the like.

In response to identifying the prescription record 118 of the patient 154 and/or authenticating the identity of the patient 154, the fulfillment module 124 may provide for dispensing the prescribed beneficial product(s) from the inventory 120 of the dispensing station 110. Dispensing may comprise the dispensing station 110 identifying one or more dispensable units 122 in the inventory 120 using a reader 119. Alternatively, or in addition, the dispensable units 122 may be placed within respective, unique storage locations (e.g., unique bins), as described below. The inventory database 116 may maintain indicators of the storage location of each dispensable unit 122. The fulfillment module 124 may query the inventory database 116 to determine the storage location of the dispensable units 122 required to fulfill the prescription.

The dispensing station 110 may further comprise a dispensing module 129 configured to dispense the identified dispensable units 122 to a patient in response to the fulfillment module 126 determining that the prescription can be fulfilled. As described below, the dispensing module 129 may be further configured to verify the beneficial products before the beneficial products are dispensed to the patient. Verifying the beneficial products may comprise using the reader 119 to re-read identifying information from the beneficial products (e.g., re-scanning a bar code, weighing one or more dispensable units 122, or the like).

Fulfilling the prescription may further comprise the fulfillment module 124 processing a payment for the prescribed beneficial products dispensed to the patient 154. The payment may be processed using credentialed payment information provided by the patient 154 (e.g., credit card, debit card, etc.) using a third-party payment service 132 accessible via the network 130. The third-party payment service 132 may include, but not limited to: a credit card processing service, a banking institution, an electronic payment service (e.g., PAYPAL®), or the like. Alternatively, or in addition, the payment may be made using a non-credentialed payment source, such as currency.

The dispensing station 110 may prevent unauthorized access to the beneficial products in the inventory 120 by, for example, authenticating the patient 154 and/or associating the patient with a prescription record 118, as described above. If the patient 154 cannot be associated with a valid prescription record 118 and/or the identity of the patient 154 is not authenticated (e.g., credentialed payment information and/or other information acquired from the patient 154 do not correspond to any prescription records 118), the dispensing station 110 may prevent beneficial products from being dispensed from the inventory 120.

As discussed above, a prescription record 118 may comprise and/or reference patient identifying information. The patient 154 may be authenticated by matching information obtained by the fulfillment module 124 with information of the prescription record 118. The information may be limited to credentialed payment information, such as a credit card number, and/or may comprise additional patient information obtained from the patient 154, as described above.

In some embodiments, unauthorized access may be prevented by assigning a TTL value to a prescription record 118. During the TTL period, the prescription record 118 is marked as "valid," and can be used to obtain beneficial products from the dispensing station 110. After the TTL expires, the prescription record 118 is marked as "invalid" and can no longer be used. The TTL may be set according to testing and experience. For example, if the dispensing station is located in close proximity to the patient 154 (e.g., in the health care provider's office 102), the TTL may be relatively short (e.g., 30 minutes to an hour). This allows the patient 154 to complete the visit with the health care provider 152 and fulfill the prescription, while making it difficult for an unauthorized person to use the prescription record 118 to obtain the prescribed beneficial products.

Alternatively, or in addition, the prescription record 118 may be associated with an identifier of one or more dispensing station(s) 110. There may be a number of different dispensing stations 110 located throughout a particular area (e.g., within a large hospital, a city-wide heath care network, etc.). The dispensing station identifier associated with the prescription record 118 may restrict fulfillment of the prescription to one or more identified dispensing stations 110 and/or to a particular locale or area. Accordingly, a person at another dispensing station in another area (not shown) may be prevented from accessing the prescribed beneficial products identified in the prescription record 118.

Figure 1B:
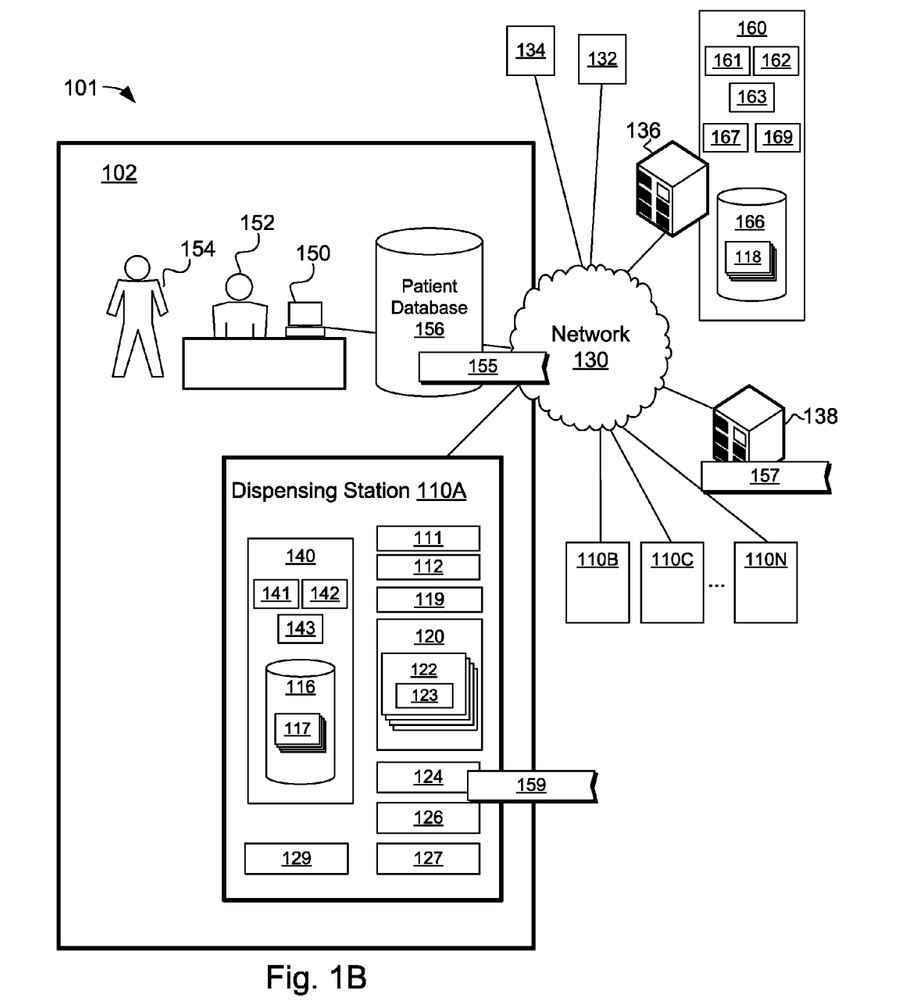
FIG. 1B is a block diagram of another embodiment of a system for dispensing beneficial products.

FIG. 1 B is a block diagram of another embodiment of a system 101 for dispensing beneficial products. The system 101 comprises a prescription record database 166 comprising prescription records 118 for patients 154 of the health care provider 152. The prescription database 166 may be implemented on the server computing device 160, which may comprise a processor 161, memory 162, non-transitory storage 163, and so on, as described above.

A prescription record import module 167 may be configured to import prescription records 118 into the prescription record database 166 in response to messages from the health care provider 152 and/or other, third-party services 138. As discussed above, in some embodiments, a patient 154 may be given the option of fulfilling a prescription at a dispensing station 110A-N. In response to the patient electing to do so, a prescription record 118 representing the prescription may be created in the prescription record database 166. In some embodiments, the prescription record 118 may be created by use of the computing system 150 of the health-care provider 152, which may comprise and/or be communicatively coupled to, the patient database 156. Generating the prescription record 118 may comprise transmitting information of the prescription record 118 to the prescription record database 166 over the network 130 (e.g., in a message 155). The prescription record import module 167 may be configured to generate a prescription record 118 in the prescription record database 166 in response to the message 155.

In some embodiments, the prescription record import module 167 may be configured to generate prescription records 118 in response to messages 157 from a third-party service, such as a health-care information broker 138. The computing system 150 of the health care provider 152 may be configured to transmit messages 155 pertaining to patient prescriptions to the health-care information broker 138. The messages 155 may be transmitted according to one or more data interchange standards, such as the standards promulgated by the National Council for Prescription Drug Programs (NCPDP®). The health-care information broker 138 may be configured to manage health-care information pertaining to the patients 154 of the health-care provider 152. In response to the message 155, the health-care information broker 138 may be configured to transmit a message 157 to the prescription record import module 167, which may generate a prescription record 118 in the prescription record database 166, as described above. In some embodiments, the computing system 150 may be configured to include additional metadata in the request 155, such as patient identifying information, references to patient identifying information, or the like. The metadata may be included in the message 157 provided to the prescription import module 166, which may be configured to incorporate the metadata into the prescription record 118.

In some embodiments, the prescription record import module 167 may be configured to authenticate and/or validate the messages 155 and/or 157, which may comprise verifying one or more digital signatures on the messages 155 and/or 157, verifying credentials associated with the messages 155 and/or 157, and so on.

As described above, after generating the prescription record 118 for the patient 154, the patient 154 may be able to fulfill the prescription at one or more of the dispensing stations 110A-N. The patent 154 may provide patient identifying information to a dispensing station 110A via the HMI module 127. In response to the patient identifying information, the fulfillment module 124 may identify a prescription record of the patient 154, which may comprise transmitting a prescription record query 159 to the server computing device 160 via the network 130. The server computing device 160 may comprise a prescription query module 169 configured to identify a prescription record 118 in the prescription database 166 in response to the query 159 and/or transmit information pertaining to the prescription record 118 to the dispensing station 110A (via the network 130). The prescription query module 169 may be configured to authenticate and/or verify the query 159, as described above (e.g., using one or more digital signatures, credentials, or the like).

In response to receiving the prescription record 118 from the server computing device 160, the fulfillment module 124 may be configured to determine whether the prescription can be fulfilled at the dispensing station 110A and dispense beneficial product(s) to the patient 154, as described above.

Figure 2A:
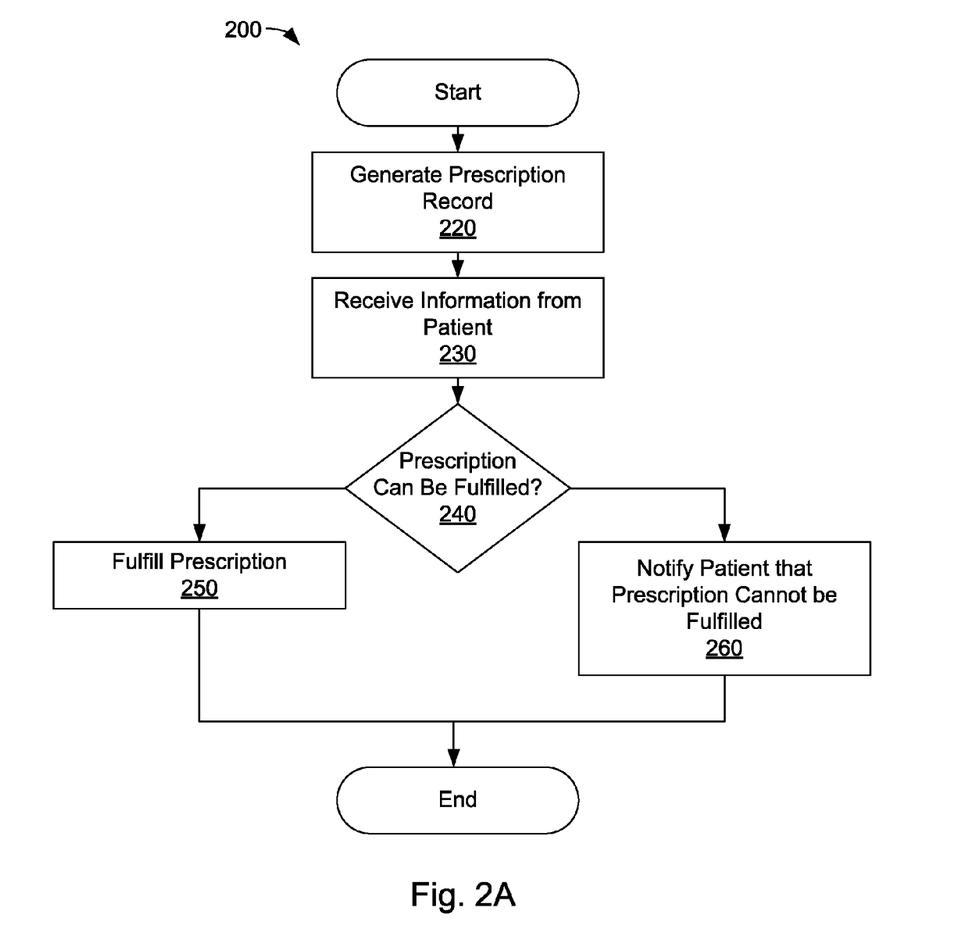
FIG. 2A is a flow diagram of one embodiment of a method for dispensing beneficial products.

FIG. 2A is a flow diagram of one embodiment of a method 200 for dispensing beneficial products. The methods disclosed herein may be implemented using a computing device comprising a processor, memory, and human-interface components (e.g., input/output devices, displays, etc.). Steps of the disclosed methods may be embodied as instructions stored on a non-transitory storage medium, such as a hard disk, optical storage media, non-volatile memory, or the like and/or may be tied to particular machine components, such as communication interfaces, HMI components, processors, non-transitory machine-readable storage media, and the like. The method 200 may, therefore, comprise loading instructions from a non-transitory storage medium, initializing machine resources, such as communication interfaces and human-machine interface components, and the like.

A health care provider, such as a doctor, may issue a prescription to a patient at step 220. Issuing a prescription may comprise the health care provider creating a prescription record that identifies the beneficial products prescribed to the patient and specifies a quantity of beneficial products prescribed to the patient. The prescription record may also include and/or reference patient identifying information, as described above. In some embodiments, the prescription record may include a TTL value, a location perimeter within which the prescription may be fulfilled, and/or may designate one or more dispensing stations at which the prescription may be fulfilled. Step 220 may comprise generating a persistent prescription record on a non-transitory storage medium, such as a database. Alternatively, or in addition, in some embodiments, step 220 may comprise generating a tangible prescription record, which may comprise a physical token or record (e.g., receipt).

Step 220 may further comprise querying an inventory database to determine whether the one or more designated dispensing stations have sufficient inventory to fulfill the prescription. When the designated dispensing stations do not have sufficient inventory, alternative dispensing stations may be identified. Alternatively, fulfillment of the prescription may be delayed until the inventory of the dispensing station(s) is restocked. When the designated dispensing stations have sufficient inventory, the inventory may be reserved for the prescription, as described above. In some implementations, a patient may be automatically notified by any suitable methodology, such as telephone, email, text message, or the like, when the inventory has been restocked and/or the prescription is available for fulfillment.

In some embodiments, step 220 comprises indicating a payment amount for the prescription. The payment amount may represent the cost to the patient to fulfill the prescription at a dispensing station. The payment amount may not include health insurance and/or other benefits. Accordingly, the prescription may be fulfilled without adjudicating the prescription through health insurance adjudication and/or coordination of benefits programs. The payment amount may be set by the health care provider, or other entity (e.g., the owner of the dispensing station).

At step 230, the dispensing station receives information from the patient attempting to fulfill the prescription. The information may comprise credentialed payment information and/or other patient identifying information, as described above.

At step 240, the dispensing station determines whether the prescription can be fulfilled (by use of the fulfillment module 124, as described above). Step 240 may comprise identifying a prescription record associated with the patient by matching information provided at step 230 with patient identifying information of a prescription record. Step 240 may further comprise prompting the patient for additional information, as described above. The additional information may be used to identify a prescription record and/or to authenticate the identity of the patient. In some embodiments, step 240 comprises verifying a TTL and/or dispensing station identifier of an identified prescription record. The prescription may be fulfilled when the TTL of the prescription record has not expired and/or the dispensing station identifier of the prescription record corresponds with the identifier (or location) of the dispensing station accessed at step 240. Step 240 may further comprise processing a payment for the prescribed beneficial product and/or verifying that the payment was successfully transferred.

If the prescription can be fulfilled, the flow continues to step 250; otherwise, the flow continues to step 260.

At step 250, the dispensing station fulfills the prescription for the patient by dispensing the prescribed beneficial products to the patient (by use of the dispensing module, as described above). Step 250 may comprise determining the storage locations of dispensable units comprising the prescribed beneficial product by querying an inventory database, and dispensing the identified dispensable units to the patient. Step 250 may further comprise validating the dispensable units in the identified storage locations using a reader (e.g., RFID reader) before the dispensing.

Step 250 may further comprise updating the inventory database to indicate that the beneficial products have been dispensed and/or updating the prescription record to indicate that the prescription has been fulfilled.

At step 260, the patient is notified that the prescription cannot be fulfilled. The notification may include the reason(s) for the failure, such as the expiration of a TTL, invalid dispensing station, payment failure, authentication failure, lack of inventory, etc. In some embodiments, the notification may direct the patient to another dispensing station, which is capable of fulfilling the prescription (e.g., has sufficient inventory to satisfy the prescription).

Figure 2B:
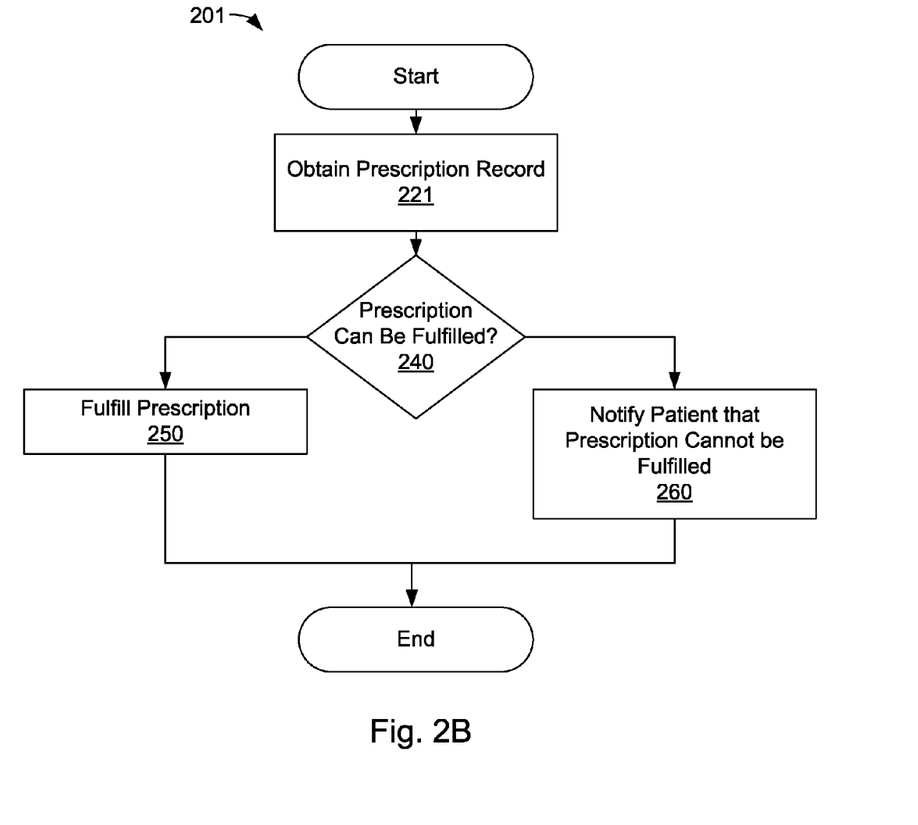
FIG. 2B is a flow diagram of another embodiment of a method for dispensing beneficial products.

FIG. 2B is a flow diagram of another embodiment of a method 201 for dispensing beneficial products. Step 221 comprises obtaining a prescription record for a patient. Step 221 may comprise acquiring patient identifying information at a dispensing station 110. Step 221 may further comprise using the patient identifying information to identify a prescription record 118 in a prescription record database 116. Alternatively, step 221 may comprise requesting a prescription record from a server computing device 160 (via a query 159 comprising the patient identifying information), as described above.

Step 240 comprises determining whether the prescription can be fulfilled at the dispensing station 110. As described above, step 240 may comprise authenticating the patient using, inter alia, the patient identifying information received at step 221, enforcing one or more restrictions of the prescription record (e.g., TTL, location, dispensing station, and so on), determining whether the dispensing station 110 has sufficient inventory to fulfill the prescription, transferring a payment for the beneficial products, and so on. If the prescription record can be fulfilled, the flow continues to step 250; otherwise, the flow continues at step 260.

Step 250 comprises fulfilling the prescription for the patent, which may comprise completing a payment for the prescription (e.g., verifying the payment of step 240), identifying beneficial products of the prescription in the inventory 120, and dispensing the beneficial products from the dispensing station 110 (via the dispensing module 129), as described above. Step 260 may comprise notifying the patient that the prescription cannot be fulfilled, as described above.

Figure 3A:
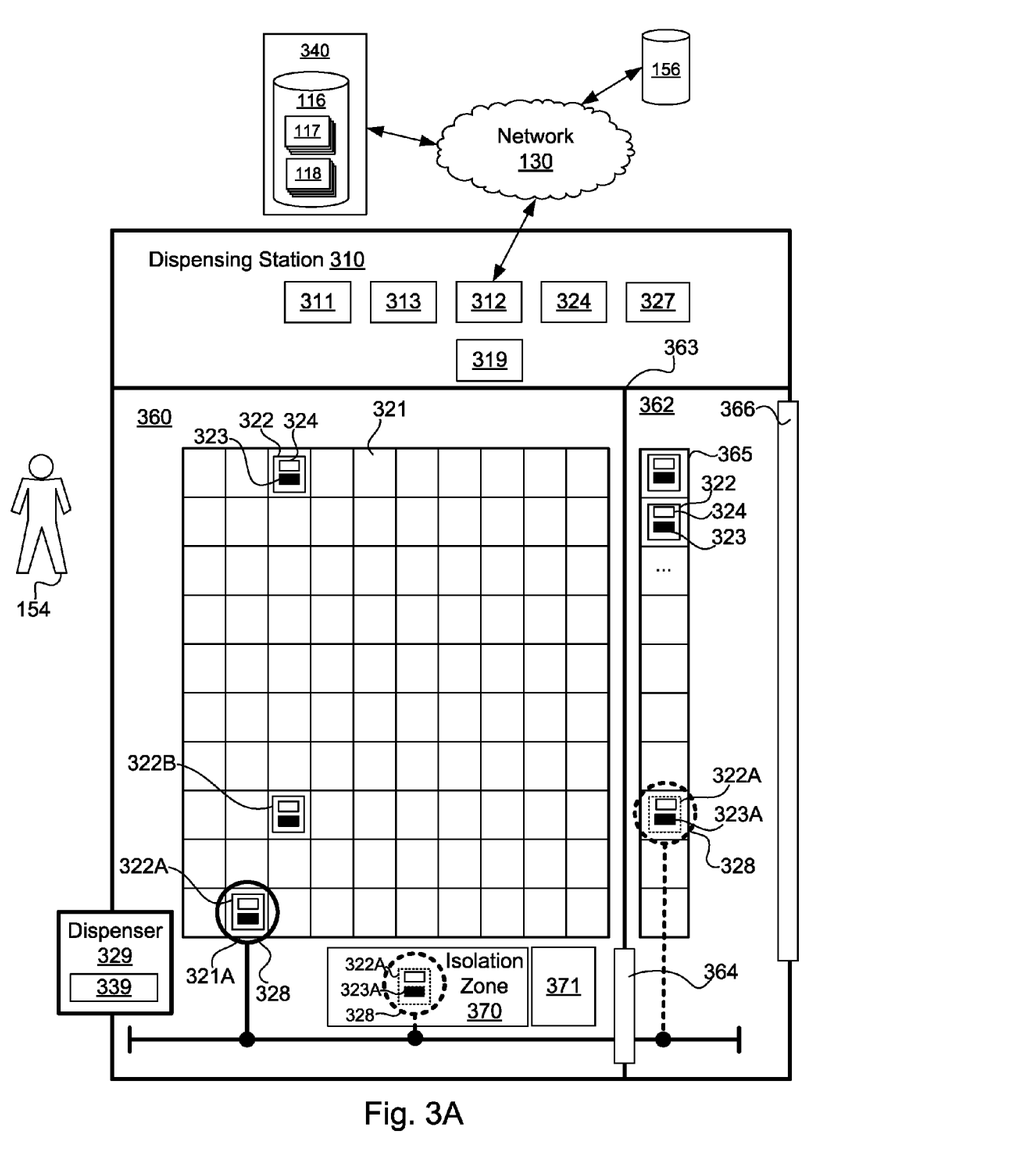
FIG. 3A is a block diagram of one embodiment of a dispensing station.

FIG. 3A depicts one embodiment of a dispensing station 310. The dispensing station 310 may comprise a controller 311, which may be configured to control the operation of the dispensing station 310. The controller 311 may comprise one or more processors, memory units, non-volatile storage devices, or the like. In some embodiments, the dispensing station comprises one or more HMI components 327, such as displays printers, keyboard inputs, or the like. The HMI components 327 may be used to acquire information from and/or present information to a patient 154.

The dispensing station comprises an inventory compartment 360 and a separate loading compartment 362. The inventory compartment 360 may be separated from the loading compartment 362 by a separator 363 and an inventory access port 364. The inventory access port 364 may be selectably opened by the controller 311. In other embodiments, new inventory may be loaded directly into the inventory compartment 360.

The inventory compartment 360 may comprise a plurality of bins 321, each configured to hold one or more dispensable units 322. Each dispensable unit 322 may comprise a respective unique identifier tag 323, as described above. Although FIG. 3A shows the bins 321 of the inventory compartment 360 arranged in a 2-dimensional grid, the disclosure is not limited in this regard and could be adapted to comprise bins 321 in any arrangement or configuration, including but not limited to a 3-dimensional grid, a cylindrical arrangement, or the like.

In some embodiments, inventory may be loaded into the dispensing station 310 through the loading access port 366. The loading access port 366 provides secure access to loading bins 365 of the loading compartment 362. Each of the loading bins 365 may be configured to receive one or more dispensable units 322, each comprising a respective unique identifier tag 323. Although FIG. 3A shows a single row of loading bins 365, the disclosure is not limited in this regard and could comprise loading bins in any arrangement or configuration.

The loading access port 366 may be secured using a suitable locking mechanism. In some embodiments, the loading access port 366 is manually accessible via a key, combination, or other secure access mechanism. Alternatively, or in addition, the loading access port 366 may be controlled by the controller 311. For example, the controller 311 may open the loading access port 366 in response to validating access credentials input via one or more HMI components 327. The access credentials may include, but are not limited to: a username, password, PIN, digital certificate, biometric, or the like. The dispensing station 310 may further comprise one or more monitoring devices 313 configured to monitor accesses to the dispensing station 310. The monitoring devices 313 may include, but are not limited to: cameras, microphones, motion detectors, or the like. The monitoring devices 313 may monitor accesses to any portion of the dispensing station 310 including, but not limited to: the inventory compartment 360, the loading compartment 362, the access ports 364 and 366, the HMI components 327, and so on. In some embodiments, the controller 311 is configured to transmit information acquired by the monitoring devices 313 via the network 130 and/or activate one or more alarms in response to detecting unauthorized access to the dispensing station 310.

In some embodiments, the controller 311 may be configured to close the inventory access port 364 while the loading access port 366 is open to prevent unauthorized access to the beneficial products in the inventory compartment 360. Accordingly, the beneficial products in the inventory compartment 360 may be secure while new inventory is being loaded into the dispensing station 310. Upon placing new inventory into the loading compartment, the loading access port 366 may be closed and/or secured.

In some embodiments, the dispensing station 310 validates the new inventory placed in the loading compartment 362. As discussed above, each dispensable unit 322 may comprise a respective unique identifier tag 323, and the dispensing station 310 may comprise one or more unique identifier tag readers 319 that are configured to read the unique identifiers therefrom. In some embodiments, the unique identifier tags 323 comprise RFID tags, and one or more of the readers 319 are configured to read the unique identifier tags 323 of all of the dispensable units 323 in the inventory compartment 360 and/or loading compartment 362. After inventory is placed in the loading compartment 362, the readers 319 may read the unique identifier tags 323 of the new dispensable units 322. The new dispensable units 322 may be identified by comparing a listing of the dispensable units 322 in the dispensing station 310 before and after loading the new inventory into the loading compartment 362. In other embodiments, the dispensing station may simply identify a number of dispensable units 322 of a particular type that are added to the station rather than uniquely identifying each unit with an RFID tag or other similar unique identifier. For example, some dispensing stations, or some sections of some dispensing stations, may be configured to dispense only units of a single kind, in which case only the number of units added must be assessed upon restocking.

The unique identifier tag readers 319 may have a limited range. Accordingly, in some embodiments, the dispensing station 310 may comprise a plurality of unique identifier tag readers 319 placed at various locations within the inventory compartment 360 and/or loading compartment 362. The placement of the plurality of unique identifier readers 319 may be configured such that the readers 319 are capable of reading unique identifier tags of all of the dispensable units 322 in the inventory and/or loading compartments 360, 362. The placements may be configured to prevent the readers 319 from reading unique identifier tags 323 within the isolation zone 370 (e.g., tag 323A), as discussed below. The controller 311 (or a selected one of the plurality of unique identifier readers 319) may combine the information acquired by each of the readers 319 to determine a complete list of the unique identifier tags 323 in the dispensing station (excluding a unique identifier tag 323A in the isolation zone 370).

Alternatively, or in addition, one or more of the unique identifier tag readers 319 may be mobile within the dispensing station 310. The mobile unique identifier tag readers 319 may move in a pre-determined movement pattern that is configured to place the readers 319 in range of each of the dispensable units 322 (and corresponding unique identifier tags 323) in the inventory compartment 360 and/or the loading compartment 362. The movement pattern may comprise an "S" pattern within the compartments 360 and/or 362. The movement pattern may be configured to prevent the one or more unique identifier tag readers 319 from reading a unique identifier tag 323A of a dispensable unit 322A within the isolation zone 370. The unique identifier readers 319 may be moved within the dispensing station 310 using any suitable mechanism. In some embodiments, one or more unique identifier readers may be placed on (and moved by) the manipulation unit 328.

In some embodiments, the controller 311 may access an inventory database 116 comprising inventory records 117 pertaining to the beneficial products of the new dispensable units 322. The inventory database 116 may operate on a computing device 340 that is accessible via the network (and communication interface 312 of the dispensing station 310) and/or may be implemented using computing resources of the dispensing station 310. The inventory in the loading compartment 362 may be compared to invoice and/or ordering information (accessible via the network 130) to validate the supply chain flow from a provider of the beneficial products to the dispensing station. For example, the controller 311 may access records 117 pertaining to the new dispensable units 322 to determine the beneficial products in the new inventory and/or verify that the new beneficial products conform with order or invoice information. In some embodiments, the dispensing station 310 generates an electronic and/or physical receipt identifying the new dispensable units 322 in the loading compartment 362.

The dispensable units 322 in the loading compartment 362 may be transferred from the loading compartment 362 to bins 321 in the inventory compartment 360. The transfers may occur when the loading access port 366 is closed and/or secured, as described above. The controller 311 may prevent the loading access port 366 from opening while inventory is transferred into the inventory compartment 360. In some embodiments, the dispensing station 310 comprises a manipulation unit 328 that is configured to transfer dispensable units 322 from the loading compartment 362 into respective bins of the inventory compartment 360. The manipulation unit 328 may be configured to access any one of the bins 321 in the inventory compartment 360 and/or loading bins 365 of the loading compartment 362. The manipulation unit 328 may be implemented using one or more electrical motors, articulators, servos, hydraulic actuators, or the like. The manipulation unit 328 may access the loading compartment 362 through the inventory access port 364 to selectively transfer dispensable units 322 in the loading bins 365 to bins 321 in the inventory compartment 360.

The dispensing station 310 may be configured to associate each dispensable unit 322 in the inventory compartment 360 with a respective bin 321. In some embodiments, these associations are established as the dispensable units 322 are transferred from the loading compartment 362 to the inventory compartment 360. The unique identifier of a dispensable unit 322 may be determined using the isolation zone 370. As used herein, an isolation zone refers to a location (or container) capable of preventing a unique identifier tag 323 from being scanned or read by the readers 319. Accordingly, when a particular dispensable unit (e.g., unit 322A) is within the isolation zone 370, the readers 319 may not be capable of reading the unique identifier tag 323A thereof. The unique identifier of the dispensable unit 322A may be determined by reading the unique identifier tags 323 of the dispensable units 322 while the unit 322A is within the isolation zone 370, and comparing these unique identifiers to unique identifiers read while the dispensable unit 322A was outside of the isolation zone 370. The unique identifier of the dispensable unit 322A may appear in the "full" set of unique identifiers and may be absent from the set of unique identifiers read while the unit 322A was in the isolation zone 370, thereby verifying its presence in the isolation zone 370.

Accordingly, in some embodiments, determining the unique identifier of the dispensable unit 322A comprises performing a first scan of the unique identifier tags of the dispensable units 322 in the dispensing station 310; placing the dispensable unit 322A into the isolation zone 370; and performing a second scan of the unique identifier tags 323 while the dispensable unit 322A is in the isolation zone 370. The unique identifier of the dispensable unit 322A may be determined by comparing the unique identifiers obtained during the first scan to the unique identifiers obtained during the second scan; the unique identifier that appears in the first scan, but not the second scan, is the unique identifier of the dispensable unit 322A.

Figure 3B:
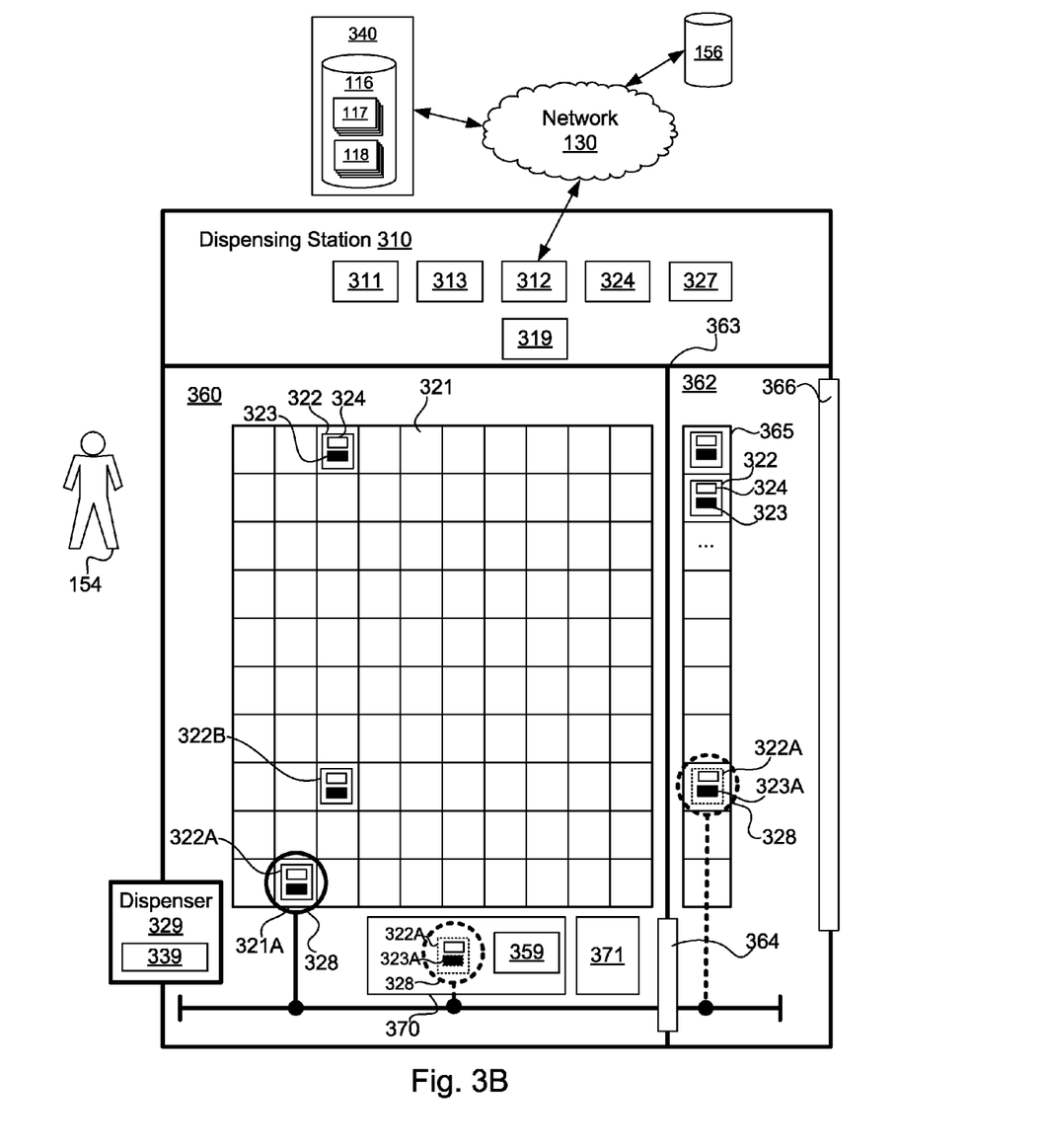
FIG. 3B is a block diagram of another embodiment of a dispensing station.

Referring to FIG. 3B, in some embodiments, the dispensing station 310 may verify the unique identifier of a particular dispensable unit 322A using a unique identifier reader 359 within the isolation zone 370. The dispensing station 310 of FIG. 3B comprises one or more unique identifier tag readers 319, which are configured to read unique identifier tags 323 of the dispensable units 322 within the dispensing station (with the exception of the isolation zone 370), as described above. The isolation zone 370 may comprise a separate unique identifier tag reader 359 that is configured to read the unique identifier tags 323 of dispensable units 322 within the isolation zone 370 (e.g., unique identifier tag 322A of unit 322A). In some embodiments, the isolation zone 370 and/or unique identifier tag reader 359 may be configured to prevent the reader 359 from reading unique identifier tags 323 of dispensable units 322 outside of the isolation zone 370.

In the FIG. 3B example, determining the unique identifier of the dispensable unit 322A may comprise placing the dispensable unit 322A within the isolation zone 370, and reading the unique identifier tag 323A using the isolation zone reader 359. Alternatively, or in addition, the unique identifier may be verified by performing a first scan of the unique identifier tags of the dispensable units 322 in the dispensing station 310 using the reader(s) 319; placing the dispensable unit 322A into the isolation zone 370; and performing a second scan of only the unique identifier tag 323A using the isolation zone unique identifier tag reader 359. The unique identifier tag 323A may be determined by comparing the first scan to the second scan and verifying that the unique identifier of the second scan appears in the first scan. Alternatively, or in addition, the second scan may comprise determining a second list of unique identifier tags using the reader(s) 319, while the dispensable unit 322A is within the isolation zone 370. The unique identifier of the dispensable unit 322A may be further verified by determining that the unique identifier of the dispensable unit 322A appears in the first list, and not in the second list, and corresponds to the unique identifier read by the separate, unique identifier reader 359.

In some embodiments, dispensable units 322 may be further verified during transfer based upon inventory information (e.g., an inventory record 117 associated with the dispensable unit 322A). For example, an inventory record 117 associated with the dispensable unit 322A may indicate that it should have a particular weight, be of a particular size, or the like. In some embodiments, the dispensing station 310 comprises one or more measurement devices 371 (e.g., scales, optical scanners, electromagnetic scanners, magnetic resonance imaging, x-ray, etc.), to verify that the dispensable unit 322A corresponds to information of its corresponding inventory record 117. Such features may be provided as secondary (or, in some embodiments, primary) means for preventing dispensing errors or, as described below, "safety checks."

In response to determining the unique identifier of the particular dispensable unit 322A (and/or verifying inventory information of the unit 322A), the manipulation unit 328 may transfer the dispensable unit 322A into a selected bin 321A of the inventory compartment 360. The controller 311 and/or inventory database 116 may be updated to associate the dispensable unit 322A with the selected bin (e.g., bin 321A).

Since the dispensing station 310 maintains information pertaining to the unique identifier and location of each dispensable unit 322, the dispensing station 310 may "serialize" the inventory of beneficial products. As used herein, inventory serialization refers to finely-grained inventory management that tracks medication by "type" (e.g., UPC code, NDC code, RxNorm, etc.) as well as manufacture date, supplier, sell-by date, expiration date, lot, packaged date and time, and so on. Accordingly, the dispensing station 310 may dispense beneficial products in a particular order and/or based upon a particular preference. For example, dispensable units 322A and 322B may both comprise the same type of beneficial product. The beneficial product in dispensable unit 322A may have an earlier "sell-by" date than the beneficial product of dispensable unit 322B. Accordingly, the dispensing station 310 may be configured to ensure that unit 322A is dispensed before dispensing 322B.

The dispensing station 310 may comprise a fulfillment module 324 to dispense beneficial products to a patient 154. The fulfillment module 324 may be configured to process a prescription request from a patient 154, which may comprise authenticating the identity of the patient 154, identifying a prescription record 118 associated with the patient 154, validating restrictions associated with the prescription record 118 (e.g., TTL, location, dispensing station identifier, etc.), processing a payment for the prescription, and so on, as described above.

Upon successfully processing the prescription request, the dispensing station 310 may dispense one or more dispensable units 322 to the patient 154. In some embodiments, the dispensing station 310 selects dispensable units 322 based upon the type of beneficial product prescribed to the patient, as indicated by the prescription record 118 (e.g., by UPC, NDC, RxNorm, or other suitable identifier). The selection may be based on inventory serialization factors, such as the age of the dispensable units 322, a "sell-by" date of the dispensable units 322, or the like.

In some embodiments, dispensing beneficial products to the patient 154 comprises one or more safety checks. As discussed above, the dispensing station 310 maintains a location (e.g., bin) of each dispensable unit 322 in the inventory compartment 360. However, the unique identifier of the selected dispensable unit 322 to be dispensed to the patient 154 may be re-verified before being dispensed. In some embodiments, the unique identifier of the selected dispensable unit 322 may be re-verified using the isolation zone 370 as described above. The reader 319 may perform a first scan of the unique identifier tags 323 of the dispensable units 322, the manipulation unit 328 may transfer the selected dispensable unit 322 into the isolation zone 370, and the reader 319 may perform a second scan of the unique identifier tags 323 while the selected dispensable unit 322 is within the isolation zone 370. The unique identifier of the selected dispensable unit 322 may be re-verified by comparing the unique identifiers obtained during the first and second scans. In some embodiments, the unique identifier tags 323 may be further verified using a reader within the isolation zone 370, as described above.

Re-verifying may further comprise verifying inventory information associated with the selected dispensable unit 322. For example, re-verification may comprise accessing an inventory record 117 in the inventory database 116 to verify that the unique identifier of the selected dispensable unit 322 corresponds with the beneficial products prescribed to the patient 154. Other properties of the selected dispensable unit 322, such as weight, size, and so on, may be verified using the measurement devices 371.

In response to re-verifying the selected dispensable unit 322, the unit 322 may be placed within a dispenser 329 for the patient 154. The dispenser 329 may comprise a secure, one-way opening in the inventory compartment 360. In some embodiments, dispensing may further comprise generating an electronic and/or physical receipt of the transaction, updating the inventory database 116 (e.g., marking the prescription record 118 as "fulfilled"), and so on. The receipt may comprise information captured by one or more of the monitoring devices 313 validating that the beneficial products were retrieved from the dispensing station 310 by the patient 154.

In some embodiments, dispensing may further comprise printing dispensing information on a label of a dispensable unit 322. The dispensing information may comprise, but is not limited to: a name of the beneficial product, usage instructions, expiration date, receipt information, health care provider contact information, and so on. The dispensing information may comprise patient-specific information, such as drug interaction warnings, patient-specific usage directions, and so on. The dispensing information may be obtained from the inventory database 116 and/or patient database 156 via the network 130, as described above.

In some embodiments, the dispenser 329 comprises a printer 339, which is configured to print dispensing information on a dispensable unit 322. The printer 339 may be configured to print the dispensing information on a printable area 324 (e.g., label) of the dispensable unit 322. In some embodiments, the printer 339 is configured to print a printable area of a label 324 and to apply the label to a dispensable unit 322.

Alternatively, or in addition, the printer 339 may be configured such that it does not require consumables, such as labels, ink, and the like. The dispensable units 322 may each have a pre-existing label (or other surface) comprising a printable area 324. The printable area 324 may be capable of being printed upon by the printer 339 without consumables, such as ink. Accordingly, the printable area 324 may comprise a heat transfer surface, an etchable surface, or other suitable printing surface. The printer 339 may print dispensing information on the printable area 324 as dispensable units 322 are dispensed to patients 154 through the dispenser 329.

Figure 4:
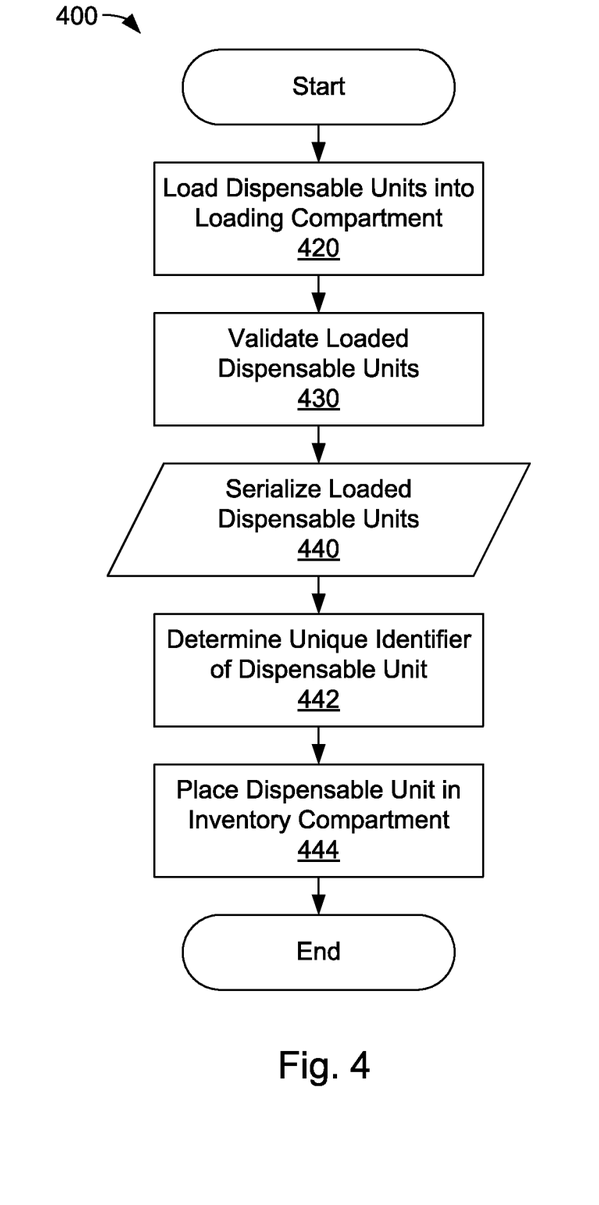
FIG. 4 is a flow diagram of one embodiment of a method for adding inventory to a dispensing station.

FIG. 4 is a flow diagram of one embodiment of a method 400 for managing an inventory of beneficial products using a dispensing station, such as the dispensing station 310 described above.

Step 420 may comprise a user (e.g., staff or other authorized personnel) accessing a loading access port of the dispensing station to place new dispensable units into one or more loading bins. Step 420 may comprise the user accessing a locking mechanism of the loading access port using an access credential and/or key. Step 420 may further comprise securing an internal, inventory access port to prevent access to existing inventory within the dispensing station. The inventory access port may selectably connect an inventory compartment of the dispensing station to a loading compartment of the dispensing station. Closing the inventory access port may allow new inventory to be loaded while beneficial products in the inventory compartment remain secure.

In some embodiments, step 420 comprises maintaining the inventory access port closed until the loading access port is closed and/or secured. Moreover, the method 400 may be configured to maintain the loading access port in a closed and/or secured configuration while the dispensable units in the loading compartment are transferred to the inventory compartment (e.g., during steps 430-444).

In some embodiments, step 420 further comprises monitoring access to the dispensing station using one or more monitoring devices (e.g., cameras, video recorders, microphones, etc.). The monitoring may continue throughout each step of the method 400. In some embodiments, opening the loading access port activates one or more monitoring devices, such as internal monitoring devices, that are adapted to monitor accesses to interior portions of the dispensing station.

At step 430, the dispensable units loaded into the loading bins may be validated. Step 430 may comprise reading the unique identifier tags of the inventory in the loading bins. In some embodiments, the unique identifier tags are read concurrently using a radio-frequency scanner, such as an RFID scanner, or the like. The unique identifiers may be used to access information about the beneficial products in the dispensable units in an inventory database. Validating the inventory may comprise comparing the unique identifiers (or inventory information) with order information to determine whether the new inventory comprises a complete order.

In some embodiments, step 430 comprises generating a physical and/or electronic receipt indicating the unique identifiers of the new inventory. The receipt may comprise additional information about the new inventory, such as beneficial product type, quantity, source, sell-by date, and so on.

In some embodiments, the validation of step 430 occurs before the dispensable units are serialized and/or transferred into the inventory compartment at steps 440-444. Alternatively, the validation of step 430 may occur at another time (e.g., after the dispensable units are transferred into the inventory compartment at steps 440-444).

The dispensable units loaded into the loading compartment may be serialized and transferred into the inventory compartment at step 440. Step 440 may comprise determining the unique identifier of each dispensable unit in the loading compartment, placing each dispensable unit in a respective bin in the inventory compartment, and updating an inventory database to associate each dispensable unit with a respective bin. Accordingly, steps 442 and 444 may be repeated for each dispensable unit in the loading compartment.

Step 442 comprises determining a unique identifier of a particular dispensable unit in the loading compartment. Step 442 may comprise performing a first scan of the unique identifier tags of the dispensable units in the dispensing station using one or more unique tag readers (e.g., RFID scanners); placing the particular dispensable unit into an isolation zone wherein its unique identifier tag cannot be scanned by the scanning device; and performing a second scan of the unique identifier tags of the dispensable units in the dispensing station while the particular dispensable unit is in the isolation zone. The unique identifier of the particular dispensable unit may be determined by comparing the unique identifiers obtained during the first scan to the unique identifiers obtained during the second scan; the unique identifier that appears in the first scan, but not the second scan is the unique identifier of the particular dispensable unit. In some embodiments, scanning the unique identifiers may comprise moving one or more unique tag readers within the dispensing station according to a movement pattern, as described above. Alternatively, or in addition, scanning the unique identifiers may comprise combining the unique identifier tags read by a plurality of unique tag readers at different positions within the dispensing station.

In some embodiments, step 442 may comprise using a unique identifier reader within the isolation zone, as described above. Accordingly, determining the unique identifier of the particular dispensable unit may comprise placing the particular dispensable unit within the isolation zone and reading the unique identifier thereof using a unique identifier reader in the isolation zone. The unique identifier may be further verified by performing first and/or second scans using other unique identifier readers, as described above.

At step 444, the particular dispensable unit is placed in one of the bins in the inventory compartment. Step 444 may further comprise updating the inventory database (or other data structure) to associate the particular dispensable unit with the bin (by bin location or some other bin identifier). This association may allow the inventory database to determine which bin the particular dispensable unit is located.

As described above, in some embodiments, the method 400 may iterate over steps 442 and 444 until all of the dispensable units in the loading compartment have been transferred into bins within the inventory compartment. The method 400 may end until new dispensable units are placed into the loading compartment.

Figure 5:
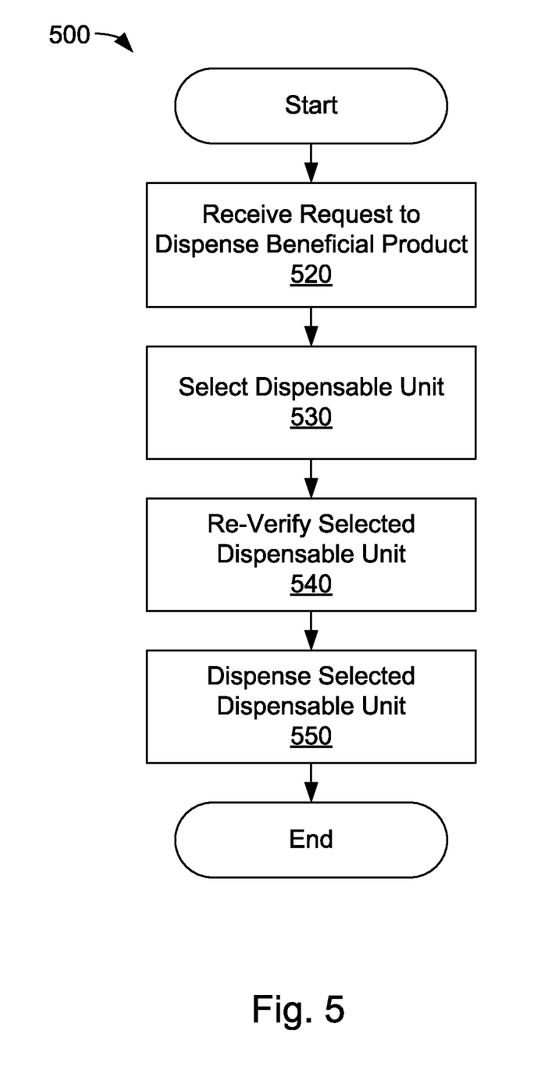
FIG. 5 is a flow diagram of one embodiment of a method for dispensing beneficial product from a dispensing station.

FIG. 5 is a flow diagram of one embodiment of a method 500 for dispensing beneficial products using a dispensing station. A request to dispense a particular beneficial product is received at step 520. The request may be received in response to a patient fulfilling a prescription at the dispensing station. Accordingly, step 520 may comprise receiving patient identifying and/or payment information and determining whether the prescription can be fulfilled, as described above in conjunction with FIGS. 2 and 3.

Step 530 comprises selecting one or more dispensable units to dispense to fulfill the request of step 520. Step 530 may comprise identifying dispensable units comprising beneficial products prescribed to the patient (based upon information in an inventory database). The selection of step 530 may also be based upon inventory serialization information, such as beneficial product sell-by date, supplier, and so on.

The selected dispensable units are transferred to a dispenser at step 540. Step 540 may comprise re-verifying the dispensable units, as described above. The re-verification may comprise verifying the unique identifier of each selected dispensable unit and/or verifying inventory information associated with each selected dispensable unit (e.g. weight, size, etc.).

In response to re-verifying the selected dispensable units, the selected dispensable units are dispensed to the patient at step 550. Step 550 may comprise transferring the selected dispensable units to a dispenser that is accessible to the patient. Step 550 may further comprise updating an inventory database to indicate that the selected dispensable units have been dispensed and are no longer in inventory, updating a prescription record to indicate that the prescription has been fulfilled, and/or generating a receipt indicating fulfillment of the prescription.

In some embodiments, step 550 may comprise printing dispensing information on the selected dispensable units, as described above. Step 550 may comprise obtaining dispensing information from an inventory and/or patient database. The selected dispensable units may comprise a pre-applied label having a printable area. The printable area may be capable of being printed upon without the use of consumables, such as ink. The method 500 may end until a next request for a beneficial product is received.

The above description provides numerous specific details for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps, or by a combination of hardware, software, and/or firmware.

Embodiments may also be provided as a computer program product including a machine-readable storage medium having stored instructions thereon that may be used to program a computer (or other electronic device) to perform processes described herein. The machine-readable storage medium may include, but is not limited to: hard drives, floppy diskettes, optical disks, CD-ROMs, DVD-ROMs, ROMs, RAMs, EPROMs, EEPROMs, magnetic or optical cards, solid-state memory devices, or other types of medium/machine-readable medium suitable for storing electronic instructions.

As used herein, a software module or component may include any type of computer instruction or computer executable code located within a memory device and/or non-transitory machine-readable storage medium. A software module may, for instance, comprise one or more physical or logical blocks of computer instructions, which may be organized as a routine, program, object, component, data structure, etc., that perform one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

It will be understood by those having skill in the art that many changes may be made to the details of the above-described embodiments without departing from the underlying principles of the invention.

We claim:

1. A method for dispensing beneficial products, comprising:
  receiving, at a dispensing station from a user, patient identifying information comprising descriptive information corresponding to a patient;
  identifying a prescription record based upon the patient identifying information received at the dispensing station;
  verifying, based on a known location of a patient at a time when a prescription is created, that the prescription of the identified prescription record can be fulfilled at the dispensing station, the verification comprising both a time-to-live restriction and a dispensing station location restriction; and
  dispensing a beneficial product of the prescription to a patient in response to verifying that the prescription record can be fulfilled.

2. The method of claim 1, wherein verifying that the prescription can be fulfilled at the dispensing station comprises authenticating the patient based on the patient identifying information received at the dispensing station.

3. The method of claim 2, wherein authenticating the patient comprises comparing the patient identifying information with patient identifying information of the prescription record.

4. The method of claim 2, wherein authenticating the patient comprises comparing the patient identifying information with patient identifying information provided by the patient to a health care provider.

5. The method of claim 2, wherein authenticating the patient comprises requesting patient identifying information from the patient.

6. The method of claim 2, wherein the patient identifying information comprises credentialed payment information.

7. The method of claim 6, wherein the credentialed payment information corresponds to a payment made by the patient to a health care provider.

8. The method of claim 6, wherein verifying that the prescription can be fulfilled comprises processing a payment for the beneficial product.

9. The method of claim 8, further comprising processing the payment using the credentialed payment information.

10. The method of claim 6, wherein the credentialed payment information comprises one or more of credit card information, debit card information, banking information, checking account information, and electronic payment information.

11. The method of claim 1, wherein verifying that the prescription can be fulfilled comprises verifying one or more restrictions of the prescription record.

12. The method of claim 1, wherein verifying that the prescription can be fulfilled comprises verifying a time-to-live restriction of the prescription record.

13. An apparatus for dispensing beneficial products, comprising:
   a dispensing station comprising an inventory of beneficial products;
   a fulfillment module configured to access a prescription record of a patent based upon patient identifying information provided at the dispending station, and to authenticate the patient using the patient identifying information and the prescription record, and wherein the fulfillment module is further configured to, based on a known location of a patient at a time when a prescription is created, enforce both a time-to-live restriction of the prescription record and a dispensing station restriction of the prescription record; and
   a dispensing module configured to dispense a beneficial product identified in the prescription record from the inventory of beneficial products.

14. The apparatus of claim 13, further comprising an inventory database configured to track the inventory of beneficial products of the dispensing station, wherein the fulfillment module is configured to verify that the inventory comprises the beneficial product identified in the prescription record.

15. The apparatus of claim 13, wherein the fulfillment module is configured to reserve the beneficial product in the inventory database.

16. The apparatus of claim 13, wherein the patient identifying information comprises credentialed payment information, and wherein the fulfillment module is configured to process a payment for the beneficial product using the credential payment information.

17. The apparatus of claim 16, wherein the fulfillment module is configured to process the payment using a third-party payment processing service.

18. A system for dispensing beneficial products, comprising:
   a prescription database configured to maintain prescription records, each prescription record identifying a beneficial product; and
   a dispensing station communicatively coupled to the prescription database, the dispensing station comprising;
   an inventory of dispensable beneficial products,
   a fulfillment module configured to identify a prescription record in the prescription database using patient identifying information received at the dispensing station, authenticate the patient based, at least in part, on the patient identifying information, verify that the inventory of the dispensing station comprises a beneficial product of the prescription record, process a payment for the beneficial product, and wherein the fulfillment module is further configured to, based on a known location of a patient at a time when a prescription is created, enforce both a time-to-live restriction of the prescription record and a dispensing station restriction of the prescription record, and
   a dispensing module configured to dispense the beneficial product from the dispensing station.

19. The system of claim 18, wherein the prescription database is configured to import prescription records into the prescription database from a third-party service.

* * * * *